(12) United States Patent
Jiang et al.

(10) Patent No.: US 11,583,248 B2
(45) Date of Patent: Feb. 21, 2023

(54) ULTRASOUND IMAGE SYSTEM AND ULTRASOUND PROBE

(71) Applicant: QISDA CORPORATION, Taoyuan (TW)

(72) Inventors: Fu-Sheng Jiang, Taoyuan (TW); Chun-Chieh Wang, New Taipei (TW)

(73) Assignee: Qisda Corporation, Taoyuan (TW)

( * ) Notice: Subject to any disclaimer, the term of this patent is extended or adjusted under 35 U.S.C. 154(b) by 118 days.

(21) Appl. No.: 16/812,352

(22) Filed: Mar. 8, 2020

(65) Prior Publication Data

US 2021/0275138 A1 Sep. 9, 2021

(51) Int. Cl.
*A61B 8/00* (2006.01)
*A61B 8/08* (2006.01)

(52) U.S. Cl.
CPC .............. *A61B 8/4209* (2013.01); *A61B 8/52* (2013.01); *A61B 8/4461* (2013.01)

(58) Field of Classification Search
CPC ....... A61B 8/4209; A61B 8/52; A61B 8/4461; G01S 15/8915
See application file for complete search history.

(56) References Cited

U.S. PATENT DOCUMENTS

| | | | | |
|---|---|---|---|---|
| 5,882,309 A * | 3/1999 | Chiao | .................. | G01S 7/52046 600/459 |
| 6,589,180 B2 * | 7/2003 | Erikson | ................ | A61B 8/4483 257/E27.006 |
| 7,963,919 B2 * | 6/2011 | Proulx | ................ | G01S 15/8925 600/447 |
| 8,345,513 B2 * | 1/2013 | Huang | .................... | A61N 7/02 367/181 |
| 10,650,621 B1 * | 5/2020 | King | ....................... | H04L 67/10 |
| 2004/0122493 A1 * | 6/2004 | Ishibashi | ................. | A61N 7/02 607/96 |
| 2013/0176816 A1 * | 7/2013 | Nakamura | ............ | G10K 11/32 367/7 |
| 2013/0253325 A1 * | 9/2013 | Call | ..................... | A61B 8/5246 600/447 |
| 2015/0029818 A1 * | 1/2015 | Endo | .................. | G01S 15/8915 367/7 |
| 2015/0305716 A1 * | 10/2015 | Rice | ..................... | A61B 8/4461 600/443 |
| 2018/0206826 A1 * | 7/2018 | Thornton | ............ | A61B 5/0095 |
| 2019/0000422 A1 * | 1/2019 | West | .................. | G01S 15/8984 |

* cited by examiner

*Primary Examiner* — Boniface Ngathi N
*Assistant Examiner* — Zainab Mohammed Aldarraji

(57) ABSTRACT

An ultrasound image system is provided. The ultrasound image system includes an ultrasound probe and a processing circuit. The ultrasound probe includes a substrate, a first transducer array and a second transducer array. The first transducer array is fixed disposed on the substrate and configured to receive a first ultrasound signal The second transducer array is fixed disposed on the substrate and configured to receive a second ultrasound signal. Each of the first transducer array and the second transducer array includes a plurality of ultrasound transducer elements arranged along a first direction. The ultrasound transducer elements of the first transducer array are interleaved with the ultrasound transducer elements of the second transducer array. The processing circuit is coupled to the first transducer array and the second transducer array and is configured to generate an ultrasound image signal according to the first ultrasound signal and the second ultrasound signal.

12 Claims, 5 Drawing Sheets

ULTRASOUND IMAGE SYSTEM AND ULTRASOUND PROBE

BACKGROUND OF THE INVENTION

1. Field of the Invention

The present invention relates to an ultrasound image system and ultrasound probe, and more particularly, to an ultrasound image system and an ultrasound probe with high image resolution.

2. Description of the Prior Art

Ultrasound is sound waves with frequencies higher than the upper audible limit of human hearing. Ultrasound waves are used in many different fields. Ultrasonic devices are used to detect objects and measure distances. For example, an ultrasound imaging system is one of the most widely used medical imaging techniques in modern medicine for medical diagnostic purposes. The ultrasound imaging technique is a cost-effective method for medical imaging. Also, the imaging ultrasound technique is non-invasive, comfortable to the patients. During the imaging operation of the ultrasound imaging system, ultrasound waves are emitted by ultrasound transducers into an object of interest and reflections of the ultrasound waves are collected by the ultrasound transducers to generate an ultrasound image. The resolution of the ultrasound imaging system usually depends on the characteristics of the ultrasound transducers. Therefore, how to design an ultrasound imaging system with high image resolution becomes an issue in the field.

SUMMARY OF THE INVENTION

In accordance with exemplary embodiments of the present invention, an ultrasound image system and an ultrasound probe with high image resolution are provided, to solve the above-mentioned problems.

According to a first aspect of the present invention, an exemplary ultrasound image system is disclosed. The exemplary ultrasound image system includes an ultrasound probe, comprising: a substrate; a first transducer array, fixed disposed on the substrate and configured to receive a first ultrasound signal; and a second transducer array, fixed disposed on the substrate, adjacent to the first transducer array and configured to receive a second ultrasound signal, wherein each of the first transducer array and the second transducer array comprises a plurality of ultrasound transducer elements arranged along a first direction, and the plurality of ultrasound transducer elements of the first transducer array are interleaved with the plurality of ultrasound transducer elements of the second transducer array; and a processing circuit, coupled to the first transducer array and the second transducer array, and configured to generate an ultrasound image signal according to the first ultrasound signal and the second ultrasound signal.

According to a second aspect of the present invention, an exemplary ultrasound probe is disclosed. The exemplary ultrasound probe includes: a substrate; a first transducer array, fixed disposed on the substrate and configured to receive a first ultrasound signal; and a second transducer array, fixed disposed on the substrate, adjacent to the first transducer array and configured to receive a second ultrasound signal, wherein each of the first transducer array and the second transducer array comprises a plurality of ultrasound transducer elements arranged along a first direction, and the plurality of ultrasound transducer elements of the first transducer array are interleaved with the plurality of ultrasound transducer elements of the second transducer array.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to . . . ". Also, the term "couple" is intended to mean either an indirect or direct electrical connection. Accordingly, if one device is coupled to another device, that connection may be through a direct electrical connection, or through an indirect electrical connection via other devices and connections.

Figure 1:
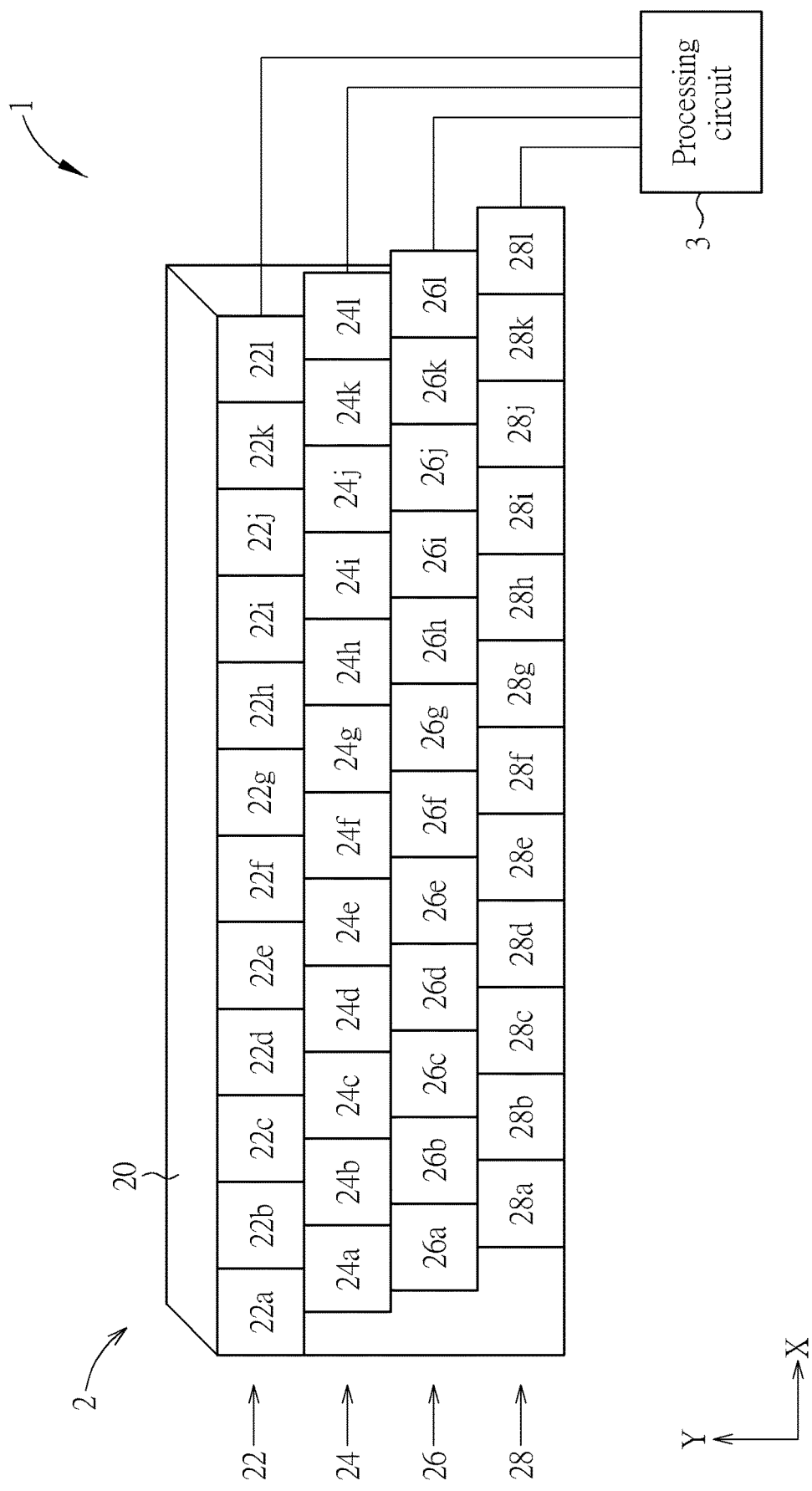
FIG. 1 is a schematic diagram of an ultrasound image system according to an embodiment of the present invention.

Please refer to FIG. 1. FIG. 1 is a schematic diagram of an ultrasound image system 1 according to an embodiment of the present invention. The ultrasound image system 1 includes an ultrasound probe 2 and a processing circuit 3. The ultrasound probe 2 includes a substrate 20 and transducer arrays 22, 24, 26 and 28. The substrate 20 may a semiconductor substrate or a complementary metal oxide semiconductor (CMOS) substrate, but not limited thereto. The transducer arrays 22, 24, 26 and 28 are fixed disposed on the substrate 20. The transducer arrays 22, 24, 26, 28 are adjacent to each other. As shown in FIG. 1, the transducer array 24 is adjacent to the transducer array 22. The transducer array 26 is adjacent to the transducer array 24 and the transducer array 24 is between the transducer array 22 and the transducer array 26. The transducer array 28 is adjacent to the transducer array 26 and the transducer array 26 is between the transducer array 24 and the transducer array 28. In an embodiment, there is no gap between two neighboring transducer arrays. For example, there is no gap between the transducer array 22 and the transducer array 24, there is no gap between the transducer array 24 and the transducer array 26, and so on. The transducer array 22 is configured to detect and receive a first ultrasound signal. The transducer array 24 is configured to detect and receive a second ultrasound signal. The transducer array 26 is configured to detect and receive a third ultrasound signal. The transducer array 28 is configured to detect and receive a fourth ultrasound signal. The processing circuit 3 is coupled to the transducer arrays 22, 24, 26 and 28. The processing circuit 3 is configured to generate an ultrasound image signal according to the first ultrasound signal and the second ultrasound signal. The processing circuit 3 can be a microprocessor control unit (MCU), a central processing unit (CPU) a microprocessor a graphics processing unit (GPU) or, a vision processing unit (VPU), but not limited thereto.

Each of the transducer array transducer arrays 22, 24, 26, 28 includes a plurality of ultrasound transducer elements arranged along a first direction. For example, as shown in FIG. 1, the transducer array 22 includes ultrasound transducer elements 22a-22l. The ultrasound transducer elements 22a-22l are arranged close to each other along an x direction. The transducer array 24 includes ultrasound transducer elements 24a-24l arranged close to each other along the x direction. The transducer array 26 includes ultrasound transducer elements 24a-24 arranged close to each other along the x direction. The transducer array 26 includes ultrasound transducer elements 26a-26l arranged close to each other along the x direction. The transducer array 28 includes ultrasound transducer elements 28a-28l arranged close to each other along the x direction. The material of the ultrasound transducer elements 22a-22l, 24a-24l, 26a-26l and 28a-28l can be a piezoelectric material, but not limited thereto. The number of the ultrasound transducer elements transducer arrays 22, 24, 26 and 28 may be varied and designed according to practical system demands. In addition, the ultrasound image system 1 further includes emitting transducer arrays (not shown in figures) configured to emit ultrasound signals.

Moreover, the ultrasound transducer elements of a first transducer array are interleaved with ultrasound transducer elements of a second transducer array adjacent to the first transducer array. For example, as shown in FIG. 1, the ultrasound transducer elements 22a-22l are interleaved with the ultrasound transducer elements 24a-24l in they direction. The ultrasound transducer elements 22a-22l and 24a-24l are disposed in a staggered and unaligned manner with respect to each other in the y direction. Similarly, the ultrasound transducer elements 24a-24l are interleaved with the ultrasound transducer elements 26a-26l in the y direction. The ultrasound transducer elements 26a-26l are interleaved with the ultrasound transducer elements 28a-28l in the y direction.

Figure 2:
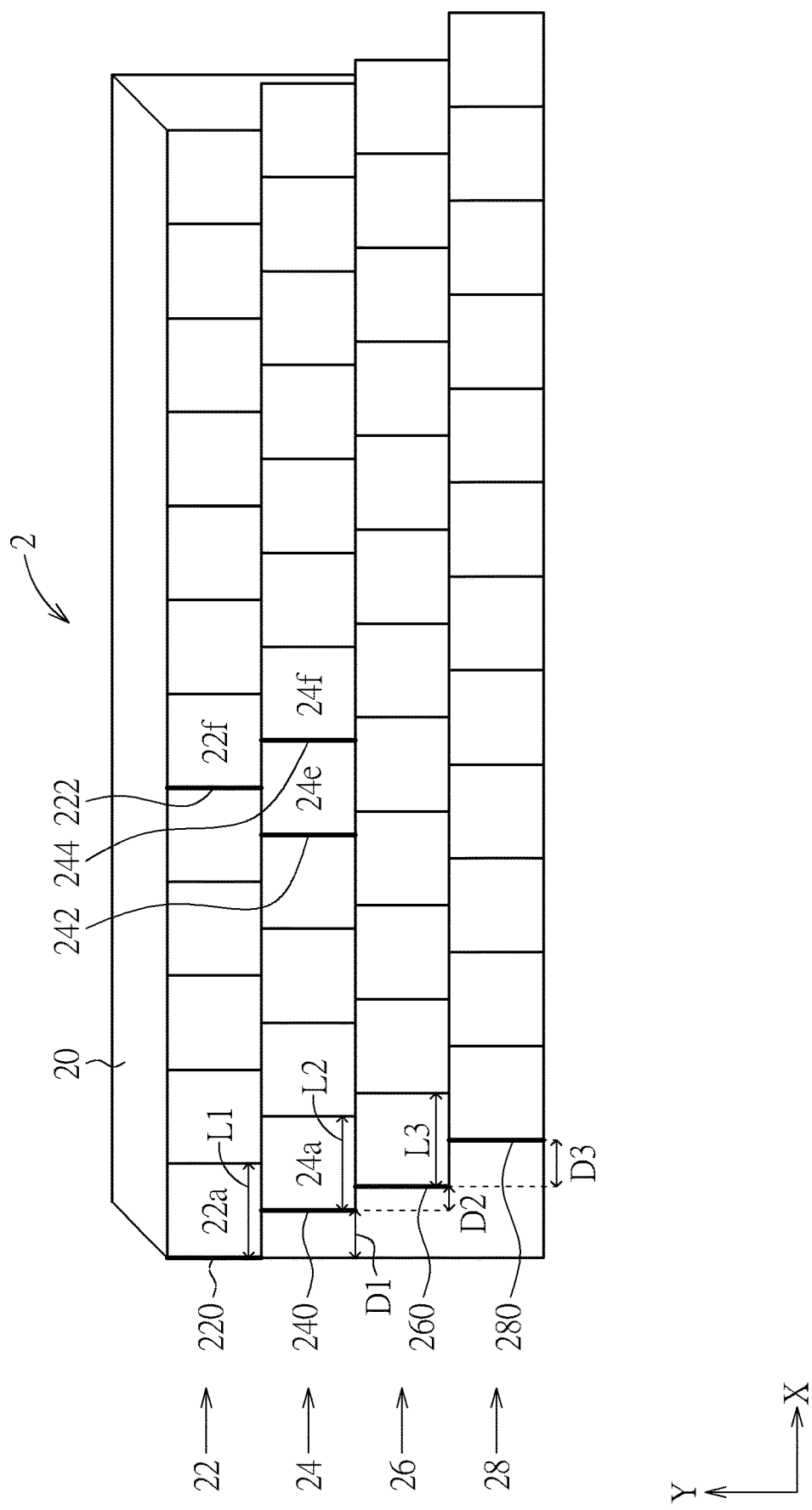
FIG. 2 is a schematic diagram illustrating the relationship between of neighboring transducer arrays according to an embodiment of the present invention.

For two neighboring arrays, a leading edge of a first ultrasound transducer element of a first transducer array extending along a second direction is not aligned with a leading edge of a first ultrasound transducer element of a second ultrasound array adjacent to the first transducer array extending along the second direction. The first ultrasound transducer element of the second ultrasound array is closest to the first transducer element of the first transducer array among the ultrasound transducer elements of the second ultrasound array. For example, as shown in FIG. 2, the ultrasound transducer element 24a is closest to the ultrasound transducer element 22a among the ultrasound transducer elements 24a-24l of the transducer array 24. A leading edge 220 of the ultrasound transducer element 22a extends along the y direction is not aligned with a leading edge 240 of the ultrasound transducer element 24a. For example, as shown in FIG. 2, the ultrasound transducer elements 24e and 24f are closest to the ultrasound transducer element 22f among the ultrasound transducer elements 24a-24l of the transducer array 24. A leading edge 222 of the ultrasound transducer element 22f extends along the y direction is not aligned with a leading edge 242 of the ultrasound transducer element 24e. Further, the leading edge 222 of the ultrasound transducer element 22a extends along the y direction is not aligned with a leading edge 244 of the ultrasound transducer element 24f.

For two neighboring arrays, a distance between the leading edge of a first ultrasound transducer element of the first transducer array and a leading edge of a first ultrasound transducer element of the second transducer array is associated with a length of the first ultrasound transducer element of the first transducer array in the first direction. For example, the distance between two leading edges of two neighboring transducer arrays can be greater than zero and smaller than the length first ultrasound transducer element of the first transducer array in the first direction. For example, the distance between the leading edge of the first ultrasound transducer element of the first transducer array and the leading edge of the first ultrasound transducer element of the second transducer array can be half, one third of, quarter, one fifth of, or sixth of the length of the first ultrasound transducer element of the first transducer array in the first direction, but not limited thereto.

As shown in FIG. 2, a distance D1 between the leading edge 220 of the ultrasound transducer element 22a and the leading edge 240 of the ultrasound transducer element 24a is associated with a length L1 of the ultrasound transducer element 22a of the transducer array 22 in the x direction. The distance D1 is greater than zero and smaller than the length L1 of the ultrasound transducer element 22a. For example, the distance D1 can be half, one third of, quarter, one fifth of, or sixth of the length L1 of the ultrasound transducer element 22a, but not limited thereto. Similarly, a distance D2 between the leading edge 240 of the ultrasound transducer element 24a and a leading edge 260 of the ultrasound transducer element 26a is associated with a length L2 of the ultrasound transducer element 24a of the transducer array 24 in the x direction. The distance D2 is greater than zero and smaller than the length L2 of the ultrasound transducer element 24a. A distance D3 between the leading edge 260 of the ultrasound transducer element 26a and a leading edge 280 of the ultrasound transducer element 28a is associated with a length L3 of the ultrasound transducer element 26a of the transducer array 26 in the x direction. The distance D3 is greater than zero and smaller than the length L3 of the ultrasound transducer element 26a.

Moreover, the ultrasound image signal can be determined by using a weighted average operation upon the image signals corresponding to respective transducer arrays. The ultrasound image signal may be calculated by the processing circuit 3 according to the following equation:

$$UIMG = \frac{\sum_{i=1}^{n} W_i * IMG_i}{\sum_{i=1}^{n} W_i} \quad (1)$$

where UIMG represents the ultrasound image signal, Tali represents a respective weighted factor of i-th image signal corresponding to i-th transducer array, IMGi represents i-th image signal corresponding to i-th transducer array, and n is positive integer.

For example, the transducer array 22 is configured to convert the first ultrasound signal detected by the transducer array 22 into a first electrical signal. The transducer array 24 is configured to convert the second ultrasound signal detected by the transducer array 24 into a second electrical signal. The transducer array 26 is configured to convert the third ultrasound signal detected by the transducer array 26 into a third electrical signal. The transducer array 28 is configured to convert the fourth ultrasound signal detected by the transducer array 28 into a fourth electrical signal. The processing circuit 3 is configured to convert the first electrical signal into an image signal IMG1, convert the second electrical signal into an image signal IMG2, convert the third electrical signal into an image signal IMG3, convert the fourth electrical signal into an image signal IMG4. The processing circuit 3 is configured to generate an ultrasound image signal UIMG according to the image signals IMG1, IMG2, IMG3 and IMG4. For example, the processing circuit 3 performs a weighted average operation on the image signals IMG1, IMG2, IMG3 and IMG4 corresponding to the transducer arrays 22, 24, 26 and 28 respectively, so as to obtain the corresponding ultrasound image signal UIMG. The processing circuit 3 calculates a weighted average of the image signals IMG1, IMG2, IMG3 and IMG4 by applying a respective weighted factor to each of the image signals IMG1, IMG2, IMG3 and IMG4 to derive the ultrasound image signal UIMG. For example, according to equation (1), the ultrasound image signal UIMG corresponding to the ultrasound image system 1 would be:

$$UIMG = \frac{W1*IMG1 + W2*IMG2 + W3*IMG3 + W4*IMG4}{W1 + W2 + W3 + W4} \quad (2)$$

where UIMG represents the ultrasound image signal, IMG1 represents the image signal corresponding to the transducer array 22, IMG2 represents the image signal corresponding to the transducer array 24, IMG3 represents the image signal corresponding to the transducer array 26, IMG4 represents the image signal corresponding to the transducer array 28, W1 represents weighted factor of the image signal IMG1 corresponding to the transducer array 22, W2 represents weighted factor of the image signal IMG2 corresponding to the transducer array 24, W3 represents weighted factor of the image signal IMG3 corresponding to the transducer array 26, W4 represents weighted factor of the image signal IMG4 corresponding to the transducer array 28.

Since each image signal corresponding to a respective transducer array includes pixel values of pixels in an image frame, the ultrasound image signal may be calculated based on pixel values of the image signals corresponding to the transducer arrays by the processing circuit 3 according to equation (1). The said pixel value can be brightness value, luminance value, hue value, chroma value, color value or any other pixel feature value. For example, for each pixel of the ultrasound image signal UIMG, a pixel value of the each pixel can be calculated according to pixel values of the image signals IMG1, IMG2, IMG3 and IMG4. According to equation (1), the pixel value of the ultrasound image signal UIMG corresponding to the ultrasound image system 1 would be:

$$UIMG\_P = \frac{W1*P1 + W2*P2 + W3*P3 + W4*P4}{W1 + W2 + W3 + W4} \quad (3)$$

where UIMG_P represents a pixel value of a selected pixel of the ultrasound image signal UIMG, P1 represents a pixel value of the selected pixel of the image signal IMG1 corresponding to the transducer array 22, P2 represents a pixel value of the selected pixel of the image signal IMG2 corresponding to the transducer array 24, P3 represents a pixel value of the selected pixel of the image signal IMG3 corresponding to the transducer array 26, P4 represents a pixel value of the selected pixel of the image signal IMG4 corresponding to the transducer array 28, W1 represents weighted factor of the image signal IMG1 corresponding to the transducer array 22, W2 represents weighted factor of the image signal IMG2 corresponding to the transducer array 24, W3 represents weighted factor of the image signal IMG3 corresponding to the transducer array 26, W4 represents weighted factor of the image signal IMG4 corresponding to the transducer array 28.

Further, the more central the transducer array is disposed, the larger the weighted factor is applied during calculation of ultrasound image signal. For example, at least one of the weighted factors W2 and W3 corresponding to the transducer arrays 24 and 26 is greater than at least one of the weighted factors W1 and W4 corresponding to the transducer array 22 and 28. For example, the weighted factor W2 corresponding to the transducer array 24 is greater than the weighted factor W3 corresponding to the transducer array 26, the weighted factor W3 corresponding to the transducer array 26 is greater than the weighted factor W4 corresponding to the transducer array 28, and the weighted factor W4 corresponding to the transducer array 28 is equal to the weighted factor W1 corresponding to the transducer array 22 (W2>W3>W4=W1). For example, the weighted factor W2 corresponding to the transducer array 24 is greater than the weighted factor W3 corresponding to the transducer array 26, the weighted factor W3 corresponding to the transducer array 26 is greater than the weighted factor W4 corresponding to the transducer array 28, and the weighted factor W4 corresponding to the transducer array 28 is greater than the weighted factor W1 corresponding to the transducer array 22 (W2>W3>W4>W1). In other words, the more central the transducer array is disposed, the larger the weighted factor is applied. Therefore, the horizontal resolution of the ultrasound image signal generated by the ultrasound image system of the present invention can be improved more effective.

Figure 3:
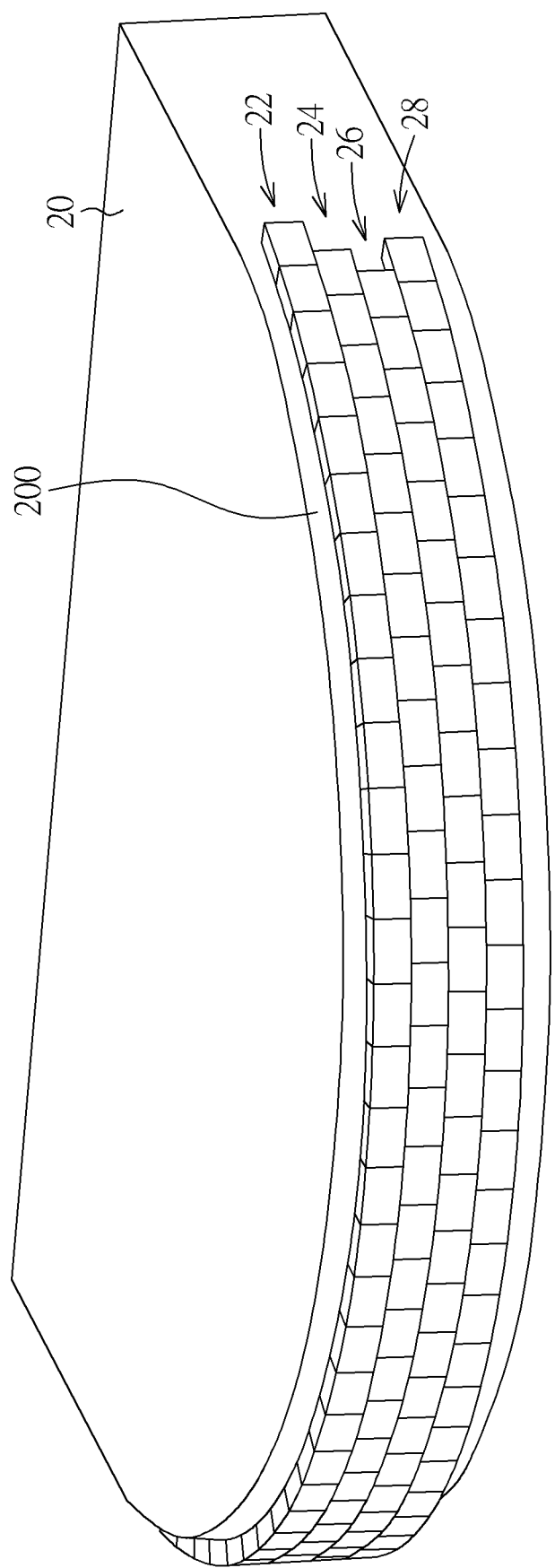
FIG. 3 is a schematic diagram illustrating transducer arrays disposed on a curved surface of the substrate according to an embodiment of the present invention.

Please refer to FIG. 3. FIG. 3 is a schematic diagram illustrating the transducer arrays disposed on a curved surface of the substrate 20 according to an embodiment of the present invention. Different from the substrate 20 having a flat surface for accommodating the transducer arrays shown in FIG. 1, the substrate 20 of the ultrasound probe 2 shown in FIG. 3 includes a curved surface 200. The transducer arrays 22, 24, 26, 28 can be fix disposed on curved surface 200. The curvature of the curved surface 200 may be varied and designed according to practical system demands.

Figure 4:
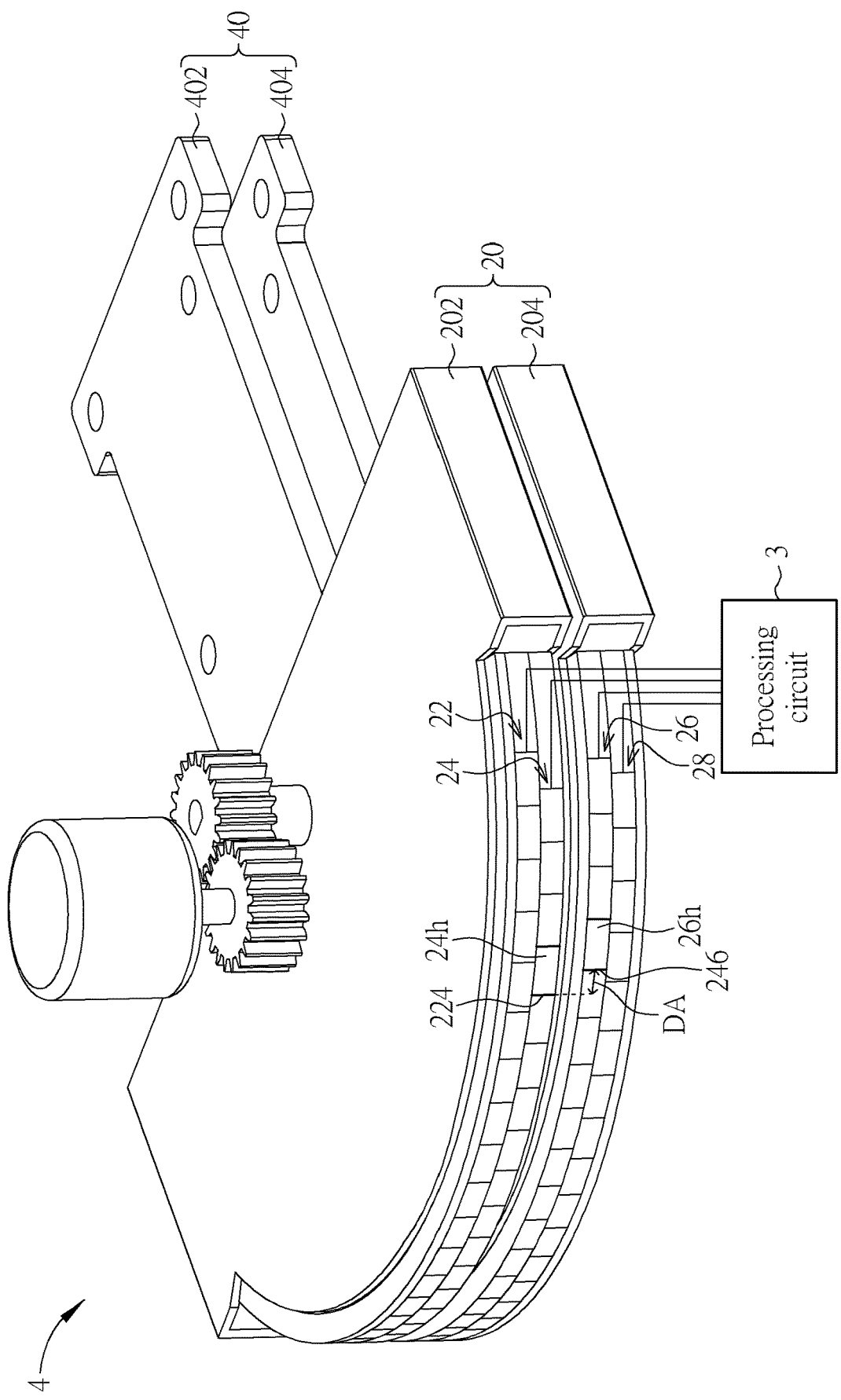
FIG. 4 is a schematic diagram of an ultrasound image system according to an alternative embodiment of the present invention.

Please refer to FIG. 4. FIG. 4 is a schematic diagram of an ultrasound image system 4 according to an embodiment of the present invention. Please note that the units in the ultrasound image system shown in FIG. 4 with the same designations as those in the ultrasound image system 1 shown in FIG. 1 have similar operations and functions, and further description thereof is omitted for brevity. The ultrasound image system 4 includes an ultrasound probe 2 and a processing circuit 3. The ultrasound probe 2 includes a substrate 20, transducer arrays 22, 24, 26 and 28, a driving assembly 40. The substrate 20 includes a first substrate 202 and a second substrate 204. As shown in FIG. 4, the transducer arrays 22 and 24 are fixed disposed on the first substrate 202. The transducer arrays 26 and 28 are fixed disposed on the second substrate 204. The driving assembly 40 includes a first driving member 402 and a second driving member 404. The first driving member 402 is connected to the first substrate 202. The second driving member 404 is connected to the second substrate 204. The driving assembly 40 is configured to drive at least one of the first substrate 202 and the second substrate 204 to move.

Figure 5:
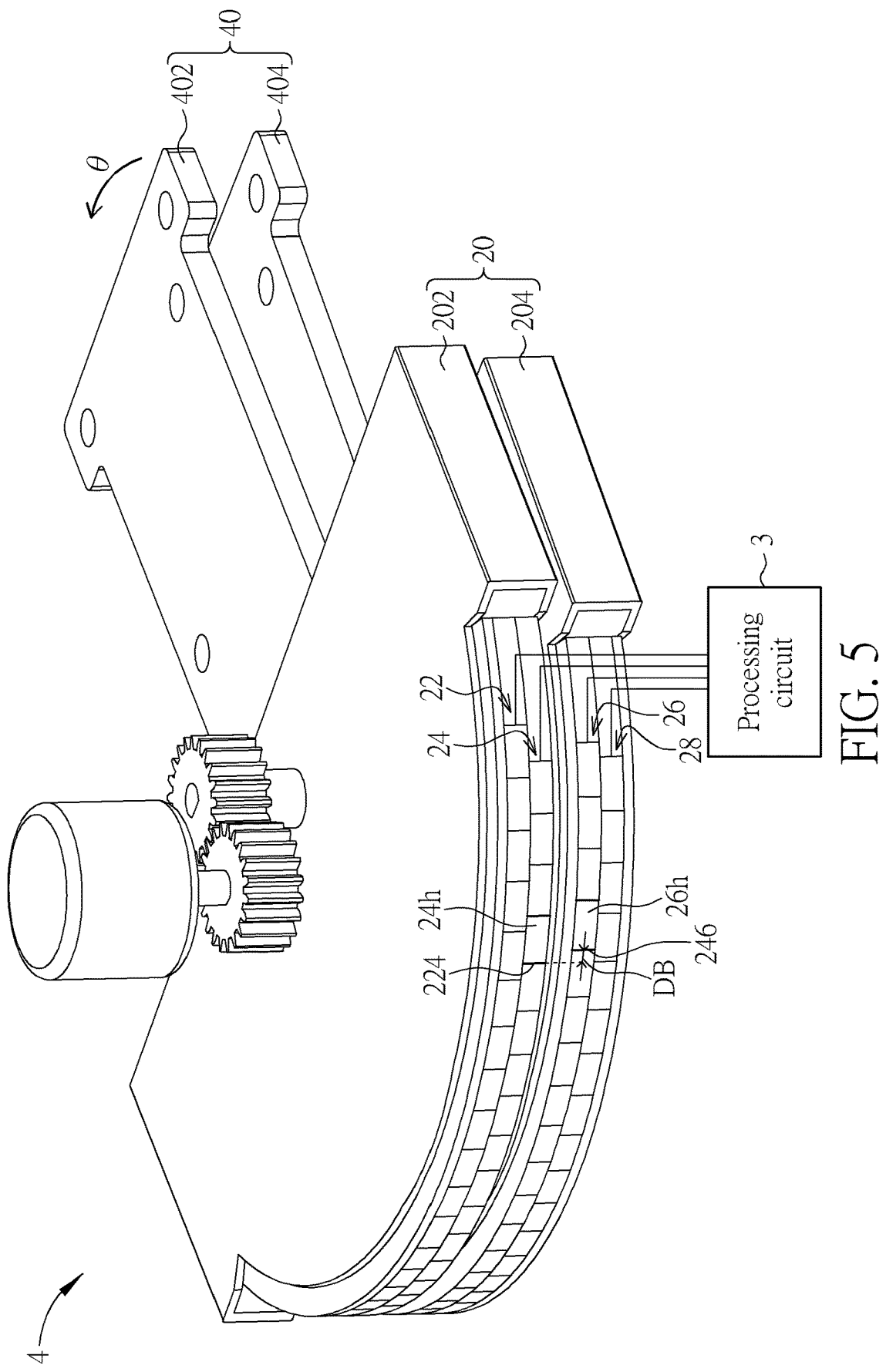
FIG. 5 is a schematic diagram illustrating operations of adjustable transducer arrays according to an embodiment of the present invention.

Further description associated with the operations of the driving assembly 40 shown in FIG. 4 follows. A user can operate the first driving member 402 (or the second driving member 404) of the driving assembly 40 to drive the first substrate 202 (or the second substrate 204) to move (rotate). When at least one of the first driving member 402 and the second driving member 404 is operated to move (rotate) by external force, the driving assembly 40 drives at least one of the first substrate 202 and the second substrate 204 to move. As such, a distance between a leading edge of a first ultrasound transducer element of a transducer array 24 disposed on the first substrate 202 and a leading edge of a first ultrasound transducer element of a transducer array 26 disposed on the second substrate 204 and adjacent to the first transducer array 24 is changed accordingly after the at least one of the first substrate 202 and the second substrate 204 is driven to move. For example, as shown in FIG. 4, the distance between a leading edge 224 of an ultrasound transducer element 24h of the transducer array 24 disposed on the first substrate 202 and a leading edge 246 of an ultrasound transducer element 26h of the transducer array 26 disposed on the second substrate 204 is DA. After the first driving member 402 is driven to rotate in the counterclockwise direction through an angle θ, the first substrate 202 is also rotated. Under such a situation, as shown in FIG. 5, the distance between the leading edge 224 of the ultrasound transducer element 24h of the transducer array 24 disposed on the first substrate 202 and the leading edge 246 of the ultrasound transducer element 26h of the transducer array 26 is DB and the distance DB different from the distance DA. In other words, the relationship between the transducer arrays disposed on the first substrate 202 and transducer arrays disposed on the second substrate 204 can be adjusted dynamically by the driving assembly 40.

To sum up, the embodiment of the present invention can apply ultrasound transducer elements arranged in a staggered and unaligned manner with respect to each other and calculate the ultrasound image signal by using weighted average method, thus significantly enhancing the image resolution, eliminating image noise and improving the image quality.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An ultrasound image system, comprising:
   an ultrasound probe, comprising:
      a substrate;
      a first transducer array, fixed disposed on the substrate and configured to receive a first ultrasound signal and convert the first ultrasound signal into a first electrical signal, wherein the first transducer array comprises a plurality of first ultrasound transducer elements arranged sequentially along a first direction;
      a second transducer array, fixed disposed on the substrate, adjacent to the first transducer array and configured to receive a second ultrasound signal and convert the second ultrasound signal into a second electrical signal, wherein the second transducer array comprises a plurality of second ultrasound transducer elements arranged sequentially along the first direction; and
      a third transducer array, adjacent to the second transducer array, wherein the second transducer array is disposed between the first transducer array and the third transducer array, the third transducer array is configured to receive a third ultrasound signal and convert the third ultrasound signal into a third electrical signal, wherein the third transducer array comprises a plurality of third ultrasound transducer elements arranged sequentially along the first direction, wherein the plurality of first ultrasound transducer elements, the plurality of second ultrasound transducer elements and the plurality of third ultrasound transducer elements are disposed in a staggered and unaligned manner with respect to each other in a second direction different from the first direction; and
   a processing circuit, coupled to the first transducer array and the second transducer array, and configured to convert the first electrical signal into a first image signal, convert the second electrical signal into a second image signal and convert the third electrical signal into a third image signal;
   wherein the processing circuit is configured to generate an ultrasound image signal by using weighted averaging with the first image signal, the second image signal and the third image signal, the processing circuit is configured to multiply first image signal with a first weighted factor to obtain a first weighted value, multiply the second image signal with a second weighted factor to obtain a second weighted value, multiply the third image signal with a third weighted factor to obtain a third weighted value, calculate an average value of the first weighted value, the second weighted value and the third weighted value and determine the calculated average value as the ultrasound image signal, wherein the second weighted factor utilized for multiplying with the second image signal which is generated from the second transducer array disposed between the first transducer array and the third transducer array is greater than the first weighted factor utilized for multiplying with the first image signal generated from the first transduce array and the third weighted factor utilized for multiplying with the third image signal generated from the third transduce array.

2. The ultrasound image system of claim 1, wherein a first one and a second one of the plurality of first ultrasound transducer elements sequentially arrange along the first direction, and a first one, a second one and a third one of the plurality of second ultrasound transducer elements sequentially arrange along the first direction, a first boundary line between the first one and the second one of the plurality of the first ultrasound transducer elements of the first transducer array extending along the second direction is not aligned with a second boundary line between the first one and the second one of the plurality of second ultrasound transducer elements of the second transducer array extending along the second direction, and the first boundary line of the first transducer array extending along the second direction is not aligned with a third boundary line between the second one and the third one of the plurality of second ultrasound transducer elements of the second transducer array extending along the second direction.

3. The ultrasound image system of claim 2, wherein a distance between the first boundary line of the first transducer array and the second boundary line of the second transducer array is associated with a length of the first ultrasound transducer element of the first transducer array in the first direction.

4. The ultrasound image system of claim 3, wherein the ultrasound probe further comprising a driving assembly and the substrate comprising:
   a first substrate, wherein the first transducer array is fixed disposed on the first substrate; and
   a second substrate, wherein the second transducer array is fixed disposed on the second substrate;
   wherein the driving assembly is connected to the first substrate and the second substrate, and configured to drive at least one of the first substrate and the second substrate to move;
   wherein when the at least one of the first substrate and the second substrate is driven to move by the driving assembly, the distance between the first boundary line of the first transducer array and the second boundary line of the second transducer array is changed.

5. The ultrasound image system of claim 1, wherein the first transducer array and the second transducer array are disposed on a curved surface of the substrate.

6. The ultrasound image system of claim 1, further comprising:
   a transmitting transducer array, configured to emit ultrasound signals.

7. An ultrasound probe, comprising:
   a substrate;
   a first transducer array, fixed disposed on the substrate and configured to receive a first ultrasound signal and convert the first ultrasound signal into a first electrical signal, wherein the first transducer array comprises a plurality of first ultrasound transducer elements arranged sequentially along a first direction;
   a second transducer array, fixed disposed on the substrate, adjacent to the first transducer array and configured to receive a second ultrasound signal and convert the second ultrasound signal into a second electrical signal, wherein the second transducer array comprises a plurality of second ultrasound transducer elements arranged sequentially along the first direction; and
   a third transducer array, adjacent to the second transducer array, wherein the second transducer array is disposed between the first transducer array and the third transducer array, the third transducer array is configured to receive a third ultrasound signal and convert the third ultrasound signal into a third electrical signal, wherein the third transducer array comprises a plurality of third ultrasound transducer elements arranged sequentially along the first direction, wherein the plurality of first ultrasound transducer elements, the plurality of second ultrasound transducer elements and the plurality of third ultrasound transducer elements are disposed in a staggered and unaligned manner with respect to each other in a second direction different from the first direction;
   wherein the first electrical signal is converted into a first image signal, the second electrical signal is converted into a second image signal, the third electrical signal is converted into a third image signal, wherein an ultrasound image signal is calculated by using weighted averaging with the first image signal, the second image signal and the third image signal, the first image signal is multiplied with a first weighted factor to obtain a first weighted value, the second image signal is multiplied with a second weighted factor to obtain a second weighted value, the third image signal is multiplied with a third weighted factor to obtain a third weighted value, an average value of the first weighted value, the second weighted value and the third weighted value is calculated by a processing circuit for acing as the ultrasound image signal, wherein the second weighted factor utilized for multiplying with the second image signal which is generated from the second transducer array disposed between the first transducer array and the second transducer array is greater than the first weighted factor utilized for multiplying with the first image signal generated from the first transduce array and the third weighted factor utilized for multiplying with the third image signal generated from the third transduce array.

8. The ultrasound probe of claim 7, wherein a first one and a second one of the plurality of first ultrasound transducer elements arrange along the first direction, and a first one, a second one and a third one of the plurality of second ultrasound transducer elements sequentially arrange along the first direction, a first boundary line between the first one and the second one of the plurality of the first ultrasound transducer elements of the first transducer array extending along the second direction is not aligned with a second boundary line between the first one and the second one of the plurality of second ultrasound transducer elements of the second transducer array extending along the second direction, and the first boundary line of the first transducer array extending along the second direction is not aligned with a third boundary line between the second one and the third one of the plurality of second ultrasound transducer elements of the second transducer array extending along the second direction.

9. The ultrasound probe of claim 8, wherein a distance between the first boundary line of the first transducer array and the second boundary line of the second transducer array is associated with a length of the first ultrasound transducer element of the first transducer array in the first direction.

10. The ultrasound probe of claim 9, further comprising:
   a first substrate, wherein the first transducer array is fixed disposed on the first substrate;
   a second substrate, wherein the second transducer array is fixed disposed on the second substrate; and
   a driving assembly, connected to the first substrate and the second substrate, configured to drive at least one of the first substrate and the second substrate to move;
   wherein when the at least one of the first substrate and the second substrate is driven to move by the driving assembly, the distance between the first boundary line of the first transducer array and the second boundary line of the second transducer array is changed.

11. The ultrasound probe of claim 7, wherein the first transducer array and the second transducer array are disposed on a curved surface of the substrate.

12. The ultrasound probe of claim 7, further comprising:
   a transmitting transducer array, configured to transmit ultrasound signals.

* * * * *